(12) United States Patent
Babler

(10) Patent No.: US 7,632,973 B2
(45) Date of Patent: Dec. 15, 2009

(54) METHODS FOR PREPARING ALDEHYDES BY SELF-ALDOL CONDENSATION

(75) Inventor: James H. Babler, Chicago, IL (US)

(73) Assignee: Loyola University of Chicago, Chicago, IL (US)

( * ) Notice: Subject to any disclaimer, the term of this patent is extended or adjusted under 35 U.S.C. 154(b) by 0 days.

(21) Appl. No.: 12/081,955

(22) Filed: Apr. 24, 2008

(65) Prior Publication Data

US 2009/0270658 A1 Oct. 29, 2009

(51) Int. Cl.
C07C 45/72 (2006.01)
(52) U.S. Cl. ...................... 568/459; 568/461
(58) Field of Classification Search ........... 568/459, 568/461
See application file for complete search history.

(56) References Cited

U.S. PATENT DOCUMENTS 2,230,591 A * 2/1941 Fischer et al. ............... 568/460
4,547,586 A 10/1985 Suzukamo et al.

FOREIGN PATENT DOCUMENTS

DE 725275 9/1942
DE 2212948 9/1973

OTHER PUBLICATIONS

Bench et al., "Proline promoted synthesis of ring-fused homodimers: self-condensation of alpha,beta-unsaturated aldehydes," *J. Org. Chem.*, 71: 9458-9463 (2006).
Cahard et al., "Regioselective addition of the prenal potassium dienolate onto alpha,beta-unsaturated aldehydes. A short access to polyenaldehydes," *Tetrahedron Lett.*, 39:7093-7096 (1998).
Duhamel et al., "A new prenylation method using the lithium enolate of prenal. Reaction with polyunsaturated aldehydes. A short access to retinal," *Tetrahedron Lett.*, 32:4499-4500 (1991).
Hong et al., "Enantioselective organocatalytic formal [3+3]-Cycloaddition of alpha,beta-unsaturated aldehydes and application to the asymmetric synthesis of (−)-isopulegol hydrate and (−)-cubebaol," *Org. Letters*, 8, 2217 (2006).
Johnson et al., "Beta-carbethoxy-gamma,gamma-diphenylvinylacetic acid," *Org. Synth.*, 30, 18 (1950).
Kann et al., "New functionalized horner-wadsworth-emmons reagents: useful building blocks in the synthesis of polyunsaturated aldehydes. A short synthesis of (±)-(E,E)-coriolic acid," *J. Org. Chem.*, 55:5312-5323 (1990).
Millar et al., "Stereospecific synthesis of the sex pheromone of the passionvine mealybug, Planococcus minor," *Tetrahedron Lett.*, 49:315-317 (2008).
Paulose et al., "Continuous hydrogenation of citral to cintronellol, geraniol, and nerol," *Chem. Abstracts*, 78:111523 (1973).
Paulose et al., "Hydrogenation of citral. II. Continuous and batch hydrogenation of citral to geraniol-nerol," *Chem. Abstracts*, 83:10440 (1975).
Phouti et al., "Catalytic hydrogenation of geraniol," *Chem. Abstracts*, 80:37307 (1973).
Retamar et al., "Safranal a partir de verbenona," *Essenze, Derivati Agrumari*, 63:407-413 (1993).
Sala et al., "Reduction of carbon-carbon double bonds and hydrogenolysis by sodium hypophosphite," *Tetrahedron Lett.*, 25:4565-4568 (1984).
Traas et al., "Vilsmeier formylation of conjugated trienes. A convenient synthesis of dehydrocitral," *Tetrahedron Lett.*, 18:2129-2132 (1977).
Venette et al., "Mini risk assessment. Passionvine mealybug: Planococcus minor (Maskell)," 1-30 (2004).
Casiraghi et al., "The vinylogous aldol reaction: a valuable, yet understated carbon-carbon bond-forming maneuver," *Chem. Rev*, 100:1929-1972 (2000).
Duhamel et al., "A new prenylation method using the lithium enolate of prenal. reaction with aldehydes and α,β-unsaturated aldehydes.," *Tetrahedron Lett.*, 32:4495-4498 (1991).
Duhamel et al. "Polyvinylogation reagents: 1-lithio-4-trimethylsiloxy-penta-1,3-diene and 1-lithio-4-ethoxy-2-methyl-buta-1,3-diene", *Tetrahedron*, 48:9237-50 (1992).
Dyakonova et al., "Alkali-catalysed self-condensation of e-Methylbut-2-enal: formation of novel rosoxide dehydro analogue", *Mendeleev Communications*, 4:88 (1994).
International Search Report and Written Opinion for International Application No. PCT/US2009/041187 (Jul. 1, 2009).
Kuhn et al. "Richard Kuhn und Christoph Grundmann: Synthese von Des-crocetin (Tetradecaheptaen-(1.3.5.7.9.11.13)-dicarbonsaure-(1.14))", *Chemische Berichte*, 70:1318-30 (1937) [Germany Only].

* cited by examiner

*Primary Examiner*—Sikarl A Witherspoon
(74) *Attorney, Agent, or Firm*—Marshall, Gerstein & Borun LLP

(57) ABSTRACT

Methods for preparing self-aldol condensation products of prenyl aldehyde (3-methyl-2-butenal) by use of an amine catalyst under weakly acidic conditions at temperatures of 10° C. or higher are disclosed. Methods are disclosed for the selective formation of α-1,2-adducts and γ-1,2-adducts of prenyl aldehyde, and for the formation of specialty compositions useful in the flavor and fragrance industries.

23 Claims, No Drawings

METHODS FOR PREPARING ALDEHYDES BY SELF-ALDOL CONDENSATION

BACKGROUND

1. Field of the Disclosure

The disclosure relates generally to methods for preparing self-aldol condensation products of α,β-unsaturated aldehydes having at least two γ-hydrogens. More specifically, the disclosure describes methods for preparing intermediates useful in the synthesis of flavoring and fragrance compounds from 3-methyl-2-butenal, also known as prenyl aldehyde. In one embodiment, (2E)-5-methyl-2-(1-methylethenyl)-2,4-hexadienal, also known as dehydrolavandulal, (1) is formed, as shown in the following formula:

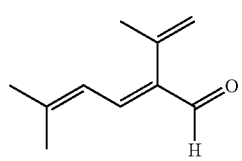

(1)

In another embodiment, (2E,4E)-3,7-dimethyl-2,4,6-octatrienal, also known as dehydrocitral, (2) is formed, as shown in the following formula:

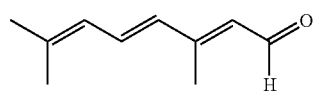

(2)

2. Brief Description of Related Technology

The known route to dehydrolavandulal (1) involves the addition of a costly reagent, 2-methyl-3-butyn-2-ol, to prenyl aldehyde under acidic conditions. Subsequent loss of water and rearrangement yields dehydrolavandulal (1), as shown in Scheme 1 (see Fisher et. al., DE 2,212,948). In contrast, the present disclosure provides cost-efficient methods for obtaining dehydrolavandulal (1) from prenyl aldehyde, via amine-catalyzed self-aldol condensation reactions.

For previous routes to dehydrocitral (2) see, e.g., Traas, et. al., *Tetrahedron Lett.*, 1977, 2129-2132. Another method of preparing dehydrocitral (2) involves the coupling of imine derivatives of prenyl aldehyde with prenyl aldehyde under weakly acidic conditions in the presence of a drying agent to obtain dehydrocitral (2), as shown in Scheme 2.

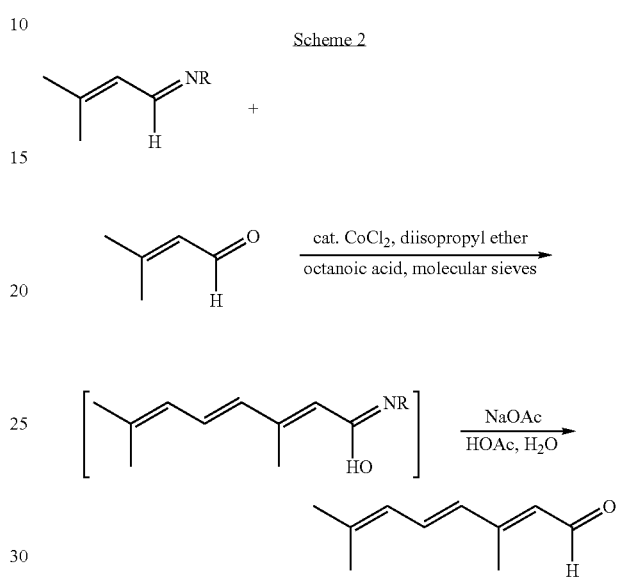

Various products can be obtained from the self-aldol condensation of prenyl aldehyde, with the particular regiochemical outcome of the reaction being determined by the specific reaction conditions. The self-aldol condensation reaction can be controlled, for example, to yield predominantly the γ-1,4-addition product, as shown in Scheme 3. For example, the γ-1,4-condensation product, 4,6,6-trimethyl-1,3-cyclohexadiene-1-carboxaldehyde (3), was exclusively obtained by reaction of the lithium dienolate of prenyl aldehyde with prenyl aldehyde in tetrahydrofuran at −70° C. to −20° C. (Duhamel et al., *Tetrahedron Lett.*, 32:4495 (1991)).

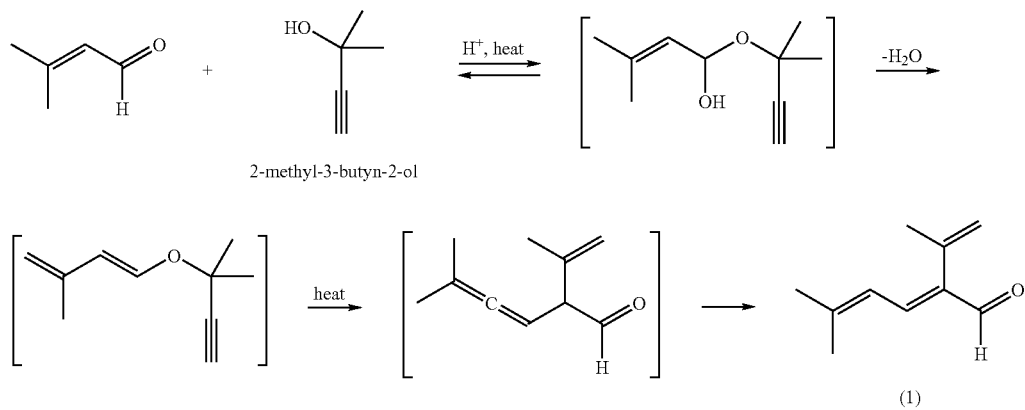

Scheme 3

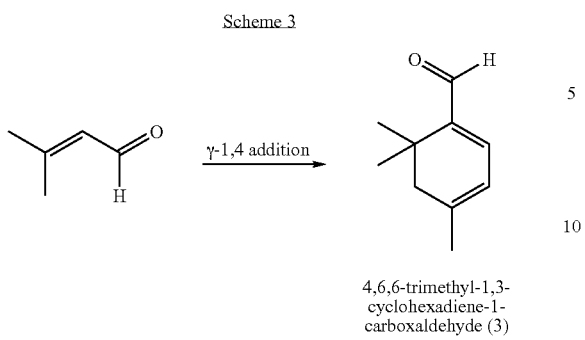

4,6,6-trimethyl-1,3-cyclohexadiene-1-carboxaldehyde (3)

At −10° C. to 0° C. (thermodynamic control), the major condensation product of the potassium dienolate of prenyl aldehyde and prenyl aldehyde is also the γ-1,4-adduct (Cahard et al., *Tetrahedron Lett.*, 39:7093-7096 (1998)). No α-adducts were detected in the crude reaction product. When the same potassium dienolate is reacted with prenyl aldehyde under kinetic control at −78° C., the major product is a mixture of cyclized and dehydrated γ-1,2-addition product, as shown in Scheme 4 (Cahard et al., *Tetrahedron Lett.*, 39:7093-7096 (1998)).

Scheme 4

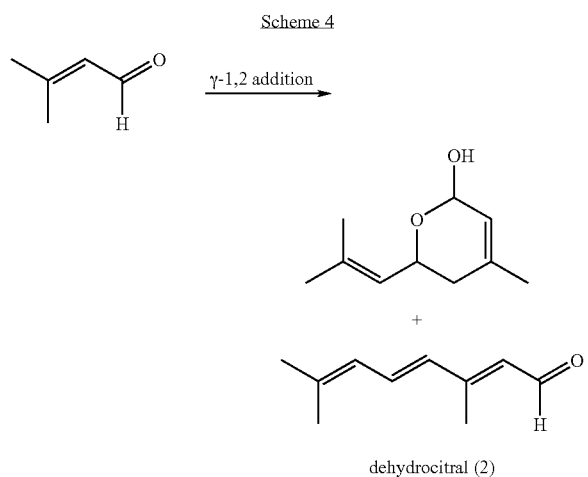

dehydrocitral (2)

In contrast to the known self-aldol reactions of prenyl aldehyde that form γ-1,4- or γ-1,2-addition products, the present disclosure provides methods for preparing α-1,2-addition products of prenyl aldehyde, as shown in Scheme 5, by use of a weak acid and a catalytic amount of a primary amine at temperatures of 10° C. or greater. The disclosure also provides methods for preparing γ-1,2-adducts of prenyl aldehyde, as shown in Scheme 4, at mild reaction temperatures of 10° C. or greater, instead of −78° C., by use of a weak acid and a catalytic amount of a secondary or tertiary amine.

Scheme 5

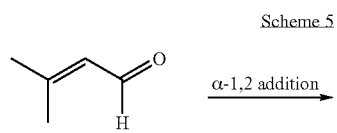

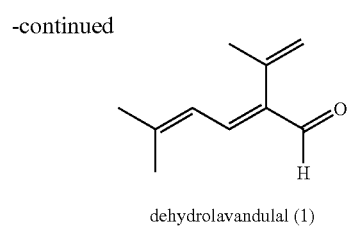

dehydrolavandulal (1)

SUMMARY

Methods are provided for preparing self-aldol condensation products of 3-methyl-2-butenal. The method involves reacting 3-methyl-2-butenal with an amine and a weak acid at a temperature of at least 10° C., for example, from about 10° C. to about 90° C. Under the conditions provided herein, the addition product formed is the 1,2-condensation product.

In one embodiment, a primary amine is used, and an α-1,2-condensation product of 3-methyl-2-butenal is formed. In another embodiment, a secondary or tertiary amine is used, and a γ-1,2-condensation product of 3-methyl-2-butenal is formed.

The weak acid can be a carboxylic acid, such as propionic acid, nonanoic acid, benzoic acid, and the like. In one embodiment, the primary amine can be an alkyl amine, such as cyclohexylamine, and also can include alkyl primary amines having tertiary alkyl groups, such as tert-octylamine, tert-butylamine, and the like. In another embodiment the secondary amine can be a dialkylamine, such as morpholine, diisobutylamine, and the like. In yet another embodiment, the tertiary amine can be a trialkylamine, such as diisopropylethylamine.

The self-aldol reaction products prepared in accordance with the present disclosure provide intermediates for the synthesis of various compounds useful as flavors and fragrances. In one embodiment, (2E)-5-methyl-2-(1-methylethenyl)-2,4-hexadienal (1), also known as dehydrolavandulal (1), can be formed. Dehydrolavandulal (1) can be reduced to lavandulol or tetrahydrolavandulol, both of which have the scent of roses and are useful in artificial lavender oils and perfumery. In another embodiment, (2E,4E)-3,7-dimethyl-2,4,6-octatrienal (2), also known as dehydrocitral (2), can be formed. Dehydrocitral (2) is the direct precursor to 2,6,6-trimethyl-1,3-cyclohexadiene-1-carboxaldehyde, also known as safranal. Safranal has the aroma of saffron, and is commercially valuable as a flavor and fragrance.

The disclosed methods avoid the use of highly corrosive acids and bases. All synthetic steps of the disclosed methods involve relatively simple transformations and generate minimal waste. The disclosed methods avoid the use of alkyl halides or organometallic reagents. In addition, aqueous work-up procedures can be minimized or eliminated.

DETAILED DESCRIPTION

The present disclosure is directed to methods for preparing self-aldol addition products (adducts) of prenyl aldehyde. The self-aldol addition products can be prepared from a reaction mixture comprising prenyl aldehyde, an amine, and a weak acid. According to the procedures disclosed herein, α-1,2-adducts and γ-1,2-adducts of prenyl aldehyde can be formed selectively. It is theorized, but not relied upon herein, that the initially formed self-aldol addition products undergo dehydration in situ to yield the self-aldol condensation products. The reaction optionally can be heated to provide a reaction temperature above room temperature. Alternatively, the reaction can be cooled to provide a reaction temperature below room temperature and at least 10° C.

In accordance with the present disclosure, the α-1,2-adduct can be obtained by the self-aldol reaction of prenyl aldehyde in the presence of a catalytic amount of a primary amine ($H_2NR^1$) and a catalytic amount of a weak acid ($RCO_2H$), wherein R is $C_1$ to $C_{17}$ alkyl, aryl, or substituted aryl, and $R^1$ is $C_3$ to $C_{12}$ alkyl or $C_4$ to $C_{12}$ cycloalkyl (Scheme 6). It is theorized, but not relied upon herein, that the initially formed α-1,2-adduct of prenyl aldehyde undergoes dehydration in situ to yield the self-aldol condensation product dehydrolavandulal (1), as shown in Scheme 6.

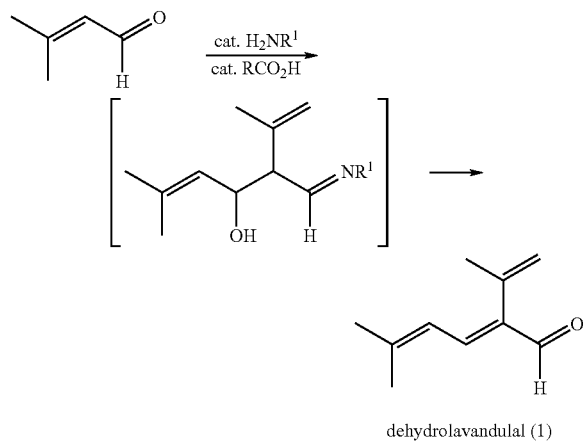

In further accordance with the present disclosure, the γ-1,2-adduct can be obtained by the self-aldol reaction of prenyl aldehyde in the presence of a catalytic amount of a secondary amine, $HNR^2R^3$, or tertiary amine, $NR^2R^3R^4$, and a catalytic amount of a weak acid $RCO_2H$, wherein R is $C_1$ to $C_{17}$ alkyl, aryl, or substituted aryl, and $R^2$, $R^3$, and $R^4$ are independently selected from $C_1$ to $C_6$ alkyl, cycloalkyl, aryl, or substituted aryl (Scheme 7). The secondary amine also can include cyclic and heterocyclic amines. Cyclic amines, for example, can include cyclic compounds comprising at least one nitrogen atom and 4 to 15 carbon atoms. Heterocyclic amines, for example, can include cyclic compounds comprising at least one nitrogen atom, 4 to 15 carbon atoms, and one to three oxygen and/or sulfur atoms. The tertiary amine can include, for example, N-substituted cyclic amines and N-substituted heterocyclic amines. Suitable N-substituents include $C_1$ to $C_3$ alkyl groups.

It is theorized, but not relied upon herein, that the initially formed γ-1,2-adduct of prenyl aldehyde undergoes dehydration in situ to yield the self-aldol condensation product dehydrocitral (2), as shown in Scheme 7.

Scheme 7

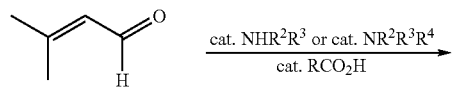

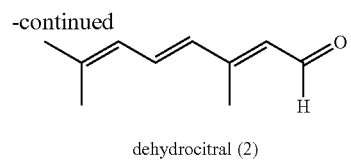

dehydrocitral (2)

The reaction can be carried out at a temperature from about 10° C. to about 90° C. Preferably, the reaction can be heated to provide a reaction temperature above room temperature. Suitable reaction temperatures include, but are not limited to, temperatures of about 30° C. to about 90° C., and about 40° C. to about 70° C. The reaction also can be carried out at temperatures in excess of 90° C. To facilitate obtaining high reaction temperatures without loss of volatile reagents, the reaction can be carried out using pressure equipment. The reaction can be carried out at room temperature, or optionally can be cooled to temperatures below room temperature and at least 10° C. Suitable reaction temperatures can include about 10° C. to about 30° C., for example, about 15° C. to about 25° C., and about 20° C.

In one embodiment, the reaction mixture includes an organic solvent or a mixture of organic solvents. The concentration of prenyl aldehyde in the solvent is determined by one skilled in the art, but typically is from about 0.5 M to about 2 M. Suitable examples of organic solvents include, but are not limited to, linear and branched alkanes, such as pentanes, hexanes, heptanes, octanes, nonanes, and decanes; cycloalkanes, such as cyclopentane, cyclohexane, methylcyclohexane, and cycloheptane; aromatic hydrocarbons, such as toluene; ethers, such as diethyl ether, diisopropyl ether, tert-butyl ethyl ether, methyl tert-butyl ether, tetrahydrofuran, 1,2-dimethoxyethane (glyme), and diethylene glycol dimethyl ether (diglyme); ketones, such as acetone, and 2-butanone; and alcohols, such as tert-butyl alcohol and 2-methyl-2-butanol (tert-amyl alcohol). Mixtures of solvents also are encompassed by the present disclosure, and use of such mixtures often improves reaction selectivity and reduces formation of by-products. Representative solvent mixtures include, but are not limited to, mixtures of heptane and tert-amyl alcohol, mixtures of octane and tert-amyl alcohol, and mixtures of tetrahydrofuran and toluene.

In another embodiment, the reaction mixture includes an optional drying agent. Suitable examples of drying agents include, but are not limited to, sodium sulfate and molecular sieves.

The reaction mixture includes a weak acid, such as a weak organic acid or a weak inorganic acid. In a preferred embodiment, the weak acid is present in the reaction mixture in a catalytic amount. As disclosed herein, a catalytic amount of the weak acid means that the molar concentration of the weak acid is less than the molar concentration of prenyl aldehyde in the reaction mixture. The molar concentration of the weak acid can be about 0.5% to about 95% of the molar concentration of prenyl aldehyde, for example, about 1% to about 50%, about 5% to about 30%, or about 10% to about 25%. Alternatively, the molar concentration of the weak acid can be slightly greater than the molar concentration of prenyl aldehyde without adversely affecting the process, as shown by Example 2.

The weak acid generally has a $pK_a$ relative to water of about 2 to about 6. In one embodiment, the weak acid includes a carboxylic acid having a $pK_a$ relative to water of about 2 to about 6. In another embodiment, the carboxylic acid includes an alkanoic acid represented by the formula $RCO_2H$, wherein R is preferably $C_1$ to $C_{17}$ alkyl, more preferably $C_1$ to $C_{10}$ alkyl, most preferably $C_1$ to $C_6$ alkyl. Suitable examples of weak alkanoic acids for use in the present disclosure include, but are not limited to, acetic acid, propionic acid, butanoic acid, pentanoic acid, hexanoic acid, heptanoic acid, octanoic acid, nonanoic acid, decanoic acid, dodecanoic acid (lauric acid), tetradecanoic acid (myristic acid), and hexadecanoic acid (palmitic acid). The carboxylic acid also includes aromatic carboxylic acids and substituted aromatic carboxylic acids. An example of an aromatic carboxylic acid is benzoic acid. Suitable aromatic carboxylic acid substituents include halides, $C_1$ to $C_3$ alkyl groups, $C_1$ to $C_3$ alkyl ethers, and the like. In another embodiment, the carboxylic acid includes an alkanedioic acid. Suitable examples of weak alkanedioic acids include hexanedioic acid (adipic acid) and tartaric acid. Another suitable weak acid is citric acid. In another embodiment, the weak acid includes a weakly acidic ion-exchange resin. Mixtures of more than one weak acid also can be used.

The reaction mixture includes an amine, such as a primary amine, secondary amine, or tertiary amine. In a preferred embodiment, the amine is present in the reaction mixture in a catalytic amount. As disclosed herein, a catalytic amount of the amine means that the molar concentration of the amine is less than the molar concentration of prenyl aldehyde in the reaction mixture. The molar concentration of the amine can be about 0.5% to about 95% of the molar concentration of prenyl aldehyde, for example, about 1% to about 50%, about 5% to about 30%, or about 10% to about 25%.

The amine can be a primary amine represented by the formula $H_2NR^1$, wherein $R^1$ is preferably $C_3$ to $C_{12}$ alkyl or $C_4$ to $C_{12}$ cycloalkyl, more preferably $C_6$ to $C_{10}$ alkyl or $C_6$ to $C_{10}$ cycloalkyl, most preferably $C_7$ to $C_9$ alkyl. In one embodiment, $R^1$ can be a secondary alkyl group, a cycloalkyl group, or a tertiary alkyl group. Suitable examples of primary amines for use in the present disclosure include, but are not limited to, 2-aminobutane, tert-butylamine, 1-methylbutylamine (also known as 2-aminopentane), 1-ethylpropylamine (also known as 3-aminopentane), 2-aminohexane, 3-aminohexane, cyclohexylamine, tert-octylamine, and mixtures thereof. Preferred primary amines include hindered amines or tertiary alkyl amines such as tert-octylamine, tert-butylamine, cyclohexylamine, and the like.

In another embodiment, the amine is a secondary amine or a tertiary amine. Suitable secondary amines can be represented by the formula $HNR^2R^3$, and suitable tertiary amines can be represented by the formula $NR^2R^3R^4$, wherein $R^2$, $R^3$, and $R^4$ are independently selected from $C_1$ to $C_6$ alkyl, cycloalkyl, aryl, or substituted aryl. The secondary amine also can include cyclic and heterocyclic amines. Cyclic amines, for example, can include cyclic compounds comprising at least one nitrogen atom and 4 to 15 carbon atoms. Heterocyclic amines, for example, can include cyclic compounds comprising at least one nitrogen atom, 4 to 15 carbon atoms, and one to three oxygen and/or sulfur atoms. The tertiary amine can include, for example, N-substituted cyclic amines and N-substituted heterocyclic amines. Suitable N-substituents include $C_1$ to $C_3$ alkyl groups. Suitable examples of secondary amines for use in the present disclosure include, but are not limited to, diethylamine, diisobutylamine, morpholine, pyrrolidine, and mixtures thereof. Suitable examples of tertiary amines for use in the present disclosure include, but are not limited to, diisopropylethylamine, triethylamine, and mixtures thereof.

The present disclosure also encompasses methods for preparing self-aldol condensation products of α,β-unsaturated aldehydes having at least two γ-hydrogens. The self-aldol condensation products can be prepared by reacting an α,β-unsaturated aldehyde having at least two γ-hydrogens in the presence of an amine and a weak acid at a temperature of at least 10° C. Suitable α,β-unsaturated aldehydes include, but are not limited to, (E)-2-butenal (crotonaldehyde), trans-2-methyl-2-butenal (tiglic aldehyde), and (E)-2-pentenal.

Synthesis of Tetrahydrolavandulol and Lavandulol from Prenyl Aldehyde

In accordance with the present disclosure, treatment of prenyl aldehyde (3-methyl-2-butenal) with a catalytic amount of a primary amine and a carboxylic acid generates dehydrolavandulal (1), as shown in Scheme 6. To obtain compounds useful as flavors and fragrances, dehydrolavandulal (1) can be converted to 2-isopropyl-5-methyl-1-hexanol (tetrahydrolavandulol) by catalytic hydrogenation, as shown in Scheme 8. Tetrahydrolavandulol has the scent of roses and is used extensively in the fragrance industry. For a previous synthesis of tetrahydrolavandulol, see Suzukamo et. al., U.S. Pat. No. 4,547,586.

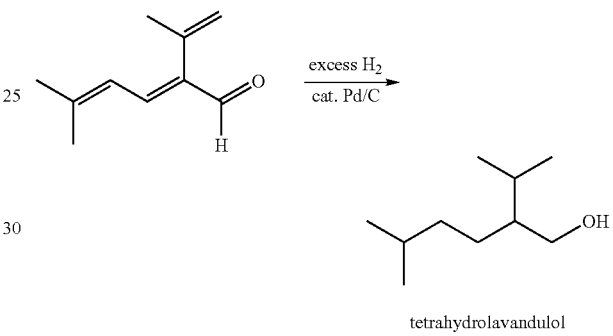

Scheme 8 tetrahydrolavandulol

Alternatively, dehydrolavandulal can be converted to (2E)-5-methyl-2-(1-methylethenyl)-2,4-hexadien-1-ol (dehydrolavandulol) with sodium borohydride in methanol, and then reduced to tetrahydrolavandulol using sodium hypophosphite hydrate and catalytic palladium on carbon, as shown in Scheme 9.

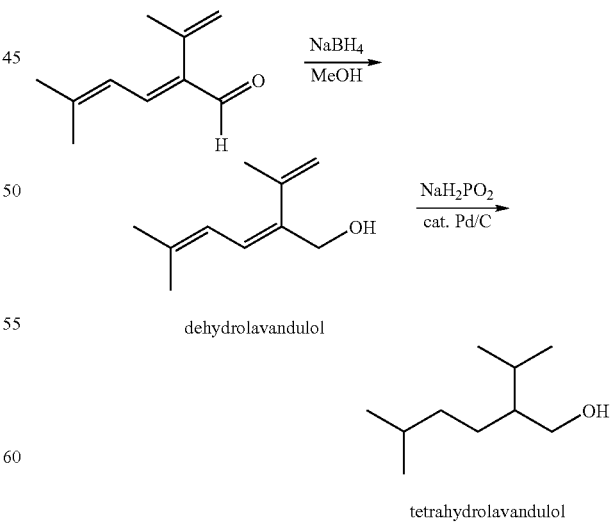

Scheme 9 dehydrolavandulol tetrahydrolavandulol

Other methods known in the art also can be used to reduce dehydrolavandulal (1) to dehydrolavandulol. For example, the selective reduction of an aldehyde to an alcohol in the presence of unsaturated carbon-carbon double bonds can be achieved by catalytic hydrogenation, as is shown for the known conversion of citral to geraniol in Scheme 10. This reduction of citral to geraniol is analogous to the conversion of dehydrolavandulal (1) to dehydrolavandulol. Suitable catalysts useful for this transformation include Fe or Zn salts with Ru compounds (see, e.g., Jpn. Kokai Tokkyo Koho 74 133, 312 (1974)), and Cu—Cr—Cd (see, e.g., Paulose et. al., *Chem. Abstracts*, 78:111523e (1973) and Paulose et. al., *Chem. Abstracts*, 83:10440w (1975)).

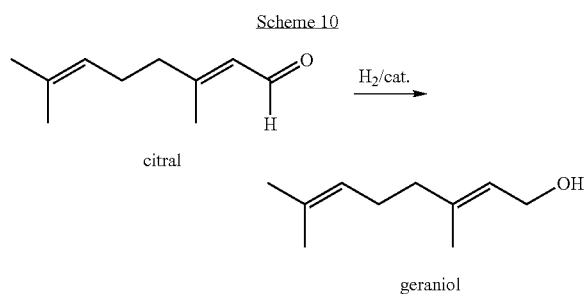

5-Methyl-2-(1-methylethenyl)-4-hexen-1-ol (lavandulol) has an herbal rose-like odor and is greatly valued in perfumery for use in artificial lavender oils. Lavandulol can be obtained by catalytic hydrogenation of dehydrolavandulol, as shown in Scheme 11.

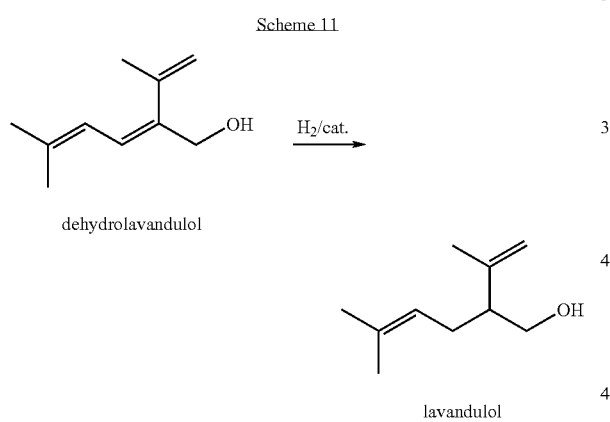

The reduction of dehydrolavandulol to lavandulol is analogous to the selective reduction of geraniol to citronellol shown in Scheme 12. Suitable catalysts useful for this selective hydrogenation include copper chromite (see, e.g., Phouti et. al., *Chem. Abstracts*, 80:37307h (1973)).

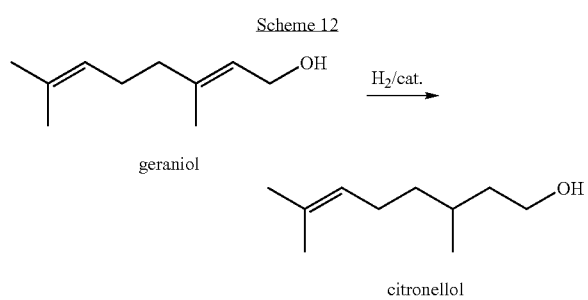

In addition to its utility in the fragrance industry, the irregular terpenoid dehydrolavandulal serves as a direct precursor to the acetate ester of (2E)-5-methyl-2-(1-methylethyl)-2,4-hexadien-1-ol, which was recently shown to be the sex pheromone of the passion vine mealybug, *Planococcus minor* (see, Millar, J. G., *Tetrahedron Lett.* 49, 315-317 (2008)). The latter insect is a significant pest of more than 250 host plants, including major crops as diverse as corn, soybeans, tomatoes, tree fruits such as oranges and lemons, rice, grapes, peanuts, coffee, cotton, and potatoes. The likelihood and severe economic consequences of this pest becoming established in the United States are discussed in Venette, R. C. and Davis, E. E., "Mini Risk Assessment. Passionvine mealybug: *Planococcus minor* (Maskell)," 1-30 (2004), which describes the potential use of pheromone-baited traps to control this invasive pest.

Synthesis of Safranal from Prenyl Aldehyde

In accordance with the present disclosure, treatment of prenyl aldehyde (3-methyl-2-butenal) with a catalytic amount of a secondary or tertiary amine and a carboxylic acid can generate dehydrocitral (2), as shown in Scheme 7. Dehydrocitral (2) can be converted to 2,6,6-trimethyl-1,3-cyclohexadiene-1-carboxaldehyde (safranal) according to the route in Scheme 13 (see, e.g., Retamar, et. al., *Essenze, Derivati Agrumari*, 63:407-413 (1993)). Safranal has the aroma of saffron, and is commercially valuable as a flavor and fragrance.

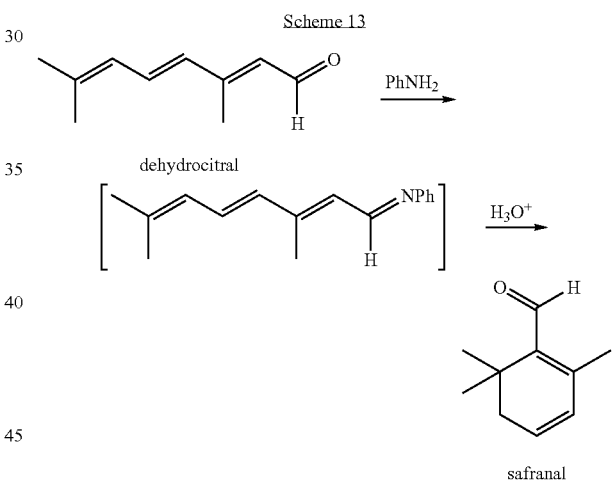

The following examples are presented for purposes of illustration and should not be construed as limiting the disclosure which is delineated in the claims.

EXAMPLES

Example 1

Preparation of (2E)-5-Methyl-2-(1-methylethenyl)-2, 4-hexadienal (1) (Dehydrolavandulal) by Self-Aldol Condensation of 3-Methyl-2-butenal (Prenyl Aldehyde) in the Presence of Benzoic Acid and Tert-octylamine at 65° C.

92 mg (1.1 mmol) of 3-methyl-2-butenal (purchased from Aldrich Chemical Co., Milwaukee, Wis.), 1.00 mL of tetrahydrofuran (99.5+%, inhibited with 25 ppm of BHT; purchased from Aldrich Chemical Co., Milwaukee, Wis.), 1.00 mL of toluene (A.C.S. reagent-grade), 16 mg of benzoic acid (0.13 mmol), 250 mg of anhydrous sodium sulfate (granular, 99+%, A.C.S. reagent), 10 μL (0.06 mmol) of tert-octylamine (purchased from Aldrich Chemical Co., Milwaukee, Wis.), and a TEFLON®-coated spin bar were added to a 25 mL, 1-neck reaction flask fitted with a reflux condenser connected to an apparatus similar to that described by Johnson and Schneider (*Org. Synth.*, 30, 18 (1950)), such that the mixture in the flask is protected from atmospheric conditions throughout the course of the reaction.

After purging the system briefly with a stream of nitrogen gas, the mixture was heated at gentle reflux (65-67° C., external oil bath temperature) for 3.5 hours. After cooling the mixture to room temperature, 5 mL of hexane and 50 mg of anhydrous potassium carbonate were added to the flask, and the mixture subsequently was stirred at room temperature for 60 minutes to neutralize the benzoic acid. The product then was isolated by filtering off any solid material through a small pad of HYFLO SUPER-CEL®, followed by removal of the volatile organic solvents by evaporation at reduced pressure. Subsequent removal of unreacted 3-methyl-2-butenal and trace amounts of tert-octylamine at room temperature under high vacuum (0.25 mmHg) afforded 21 mg of a mixture of products, the identity and ratio of which were ascertained by proton NMR analysis (recorded in $CDCl_3$ solution at 300 MHz).

After comparison of the proton NMR spectral data to published spectral data for dehydrocitral (2) (Kann et al., *J. Org. Chem.* 55, 5312-5323 (1990)) and 4,6,6-trimethyl-1,3-cyclohexadiene-1-carboxaldehyde (3) (Hong et al., *Org. Letters*, 8, 2217 (2006)), the mixture was shown to contain dehydrolavandulal (1), (2E,4E)-3,7-dimethyl-2,4,6-octatrienal (2) (dehydrocitral), and 4,6,6-trimethyl-1,3-cyclohexadiene-1-carboxaldehyde (3) in a 76:12:12 ratio, respectively. The proton NMR spectrum of dehydrolavandulal (1) exhibited a singlet at δ 9.44 (CH=O); a doublet (J=12 Hz) at δ 7.10 (vinyl H at $C_3$); a broad doublet (J=12 Hz) at δ 6.35 (vinyl H at $C_4$); broad singlets at δ 5.27 and δ 4.80 (C=$CH_2$); and broad singlets at δ 1.97, 1.94, and 1.90 (three $CH_3$ groups). The proton NMR spectrum of dehydrocitral (2) was characterized by a doublet (J=8.1 Hz) at δ 10.10 (CH=O, E stereoisomer); a doublet of doublets (J=15, 11 Hz) at δ 6.97 (vinyl H at $C_5$); a doublet (J=15 Hz) at δ 6.24 (vinyl H at $C_4$); a broad doublet (J=11 Hz) at δ 6.00 (vinyl H at $C_6$); a broad doublet (J=8.1 Hz) at δ 5.95 (vinyl H at $C_2$); a doublet (J=1.2 Hz) at δ 2.30 ($CH_3$ at $C_3$); and overlapping broad singlets at δ 1.88 (two $CH_3$ groups at $C_7$). The assignment of dehydrolavandulal was further confirmed by hydrogenation of dehydrolavandulal to obtain the known compound tetrahydrolavandulol, as shown in Example 5. The presence of 4,6,6-trimethyl-1,3-cyclohexadiene-1-carboxaldehyde as a minor component in the product mixture was indicated by a singlet at δ 9.40 (CH=O) and a singlet at δ 1.20 (6H; two $CH_3$ groups at $C_6$). For a full spectral characterization of the latter cyclic aldehyde, see B. C. Hong, et al., *Org. Letters*, 8, 2217 (2006).

A substantial amount (approximately 70% of the entire products) of the N-tert-octyl imine derivative of 3-methyl-2-butenal was isolated, and the imine was characterized by a proton NMR spectrum having a doublet (J=9.3 Hz) at δ 8.14 (CH=N); a doublet of quartets (J=9.3, 1.2 Hz) at δ 6.03 (vinyl H at $C_2$); doublets (J=1.2 Hz) at δ 1.92 and δ 1.87 (two vinyl $CH_3$ groups); a singlet at δ 1.63 ($CH_2$); a singlet at δ 1.24 (6H; NC($CH_3$)$_2$); and a singlet at δ 0.92 [9H; C($CH_3$)$_3$]. Comparison to the proton NMR spectrum of an authentic sample prepared from 3-methyl-2-butenal and tert-octylamine confirmed the identity of the imine derivative.

Without subscribing to any particular mechanism, the N-tert-octyl imine derivative of 3-methyl-2-butenal may be an "intermediate" in the self-aldol reaction process. As reaction time is increased, and the reaction proceeds to a greater percent conversion, the presence of the imine derivative in the reaction product diminishes.

Increasing the temperature of the reaction also increased the rate of reaction. A similar mixture of polyenals was obtained when the procedure of Example 1 was repeated at a temperature of approximately 80° C. using solvents including, for example, 3:1 (v/v) cyclohexane:toluene or 1:1 (v/v) 2-butanone:cyclohexane.

A primary amine catalyst is essential for the reaction to proceed. When the procedure of Example 1 was repeated in the absence of tert-octylamine, virtually no polyenals were obtained via self-aldol condensation of 3-methyl-2-butenal, as determined by proton NMR analysis of the crude reaction product. Replacement of tert-octylamine with an equivalent catalytic amount of cyclohexylamine (a less hindered primary amine) resulted in formation of self-aldol products of 3-methyl-2-butenal, although the reaction occurred at a slower rate. In addition, the presence of a drying agent (e.g., anhydrous $Na_2SO_4$) is optional for this self-aldol condensation.

Example 2

Preparation of (2E)-5-Methyl-2-(1-methylethenyl)-2,4-hexadienal (1) (Dehydrolavandulal) by Self-Aldol Condensation of 3-Methyl-2-butenal (Prenyl Aldehyde) in the Presence of Propionic Acid, Tert-Octylamine, and Molecular Sieves at 20° C.

91 mg (1.1 mmol) of 3-methyl-2-butenal; 0.50 mL of heptane; 0.50 mL of 2-methyl-2-butanol (tert-amyl alcohol); a trace of the antioxidant BHT ("butylated hydroxy toluene"); 0.10 mL (1.34 mmol) of propionic acid (99+%; purchased from Aldrich Chemical Co., Milwaukee, Wis.); 4 Å molecular sieves (22 mg; purchased from Fisher Scientific and crushed with a mortar and pestle prior to use); and 10 microliters (0.06 mmol) of tert-octylamine were added to a stoppered 10 mL, 1-neck reaction flask containing a TEFLON®-coated spin bar. This mixture subsequently was stirred at room temperature for 19 hours, after which it was diluted with 8 mL of hexane and filtered through a small pad of HYFLO SUPER-CEL® to remove the molecular sieves. 300 mg of anhydrous potassium carbonate was added to the filtrate, which subsequently was stirred at room temperature for 30 minutes to neutralize propionic acid. The product then was isolated by filtering off any solid material through a small pad of HYFLO SUPER-CEL®, followed by removal of the volatile organic solvents by evaporation at reduced pressure. Subsequent removal of unreacted 3-methyl-2-butenal at room temperature under high vacuum afforded 20 mg of a mixture of products, the identity and ratio of which were ascertained by proton NMR analysis (recorded in $CDCl_3$ solution at 300 MHz).

The polyenal mixture consisted of dehydrolavandulal (1), dehydrocitral (2), and 4,6,6-trimethyl-1,3-cyclohexadiene-1-carboxaldehyde (3) in a 86:7:7 ratio, respectively. Furthermore, the product mixture contained less of the N-tert-octyl imine derivative of 3-methyl-2-butenal compared to the reaction in Example 1 (approximately 50% of the product compared to 70% of the product in Example 1).

The above procedure was repeated using 27 mg of anhydrous sodium sulfate (granular) in place of 4 Å molecular sieves as the drying agent. Under these conditions, the same "product selectivity" (i.e., ratio of polyenals) was obtained. However, the self-aldol process proceeded more slowly when sodium sulfate was used as the drying agent compared to molecular sieves. A drying agent is not essential for the reaction however, because the aldol process slowly occurred in the absence of any added drying agent.

Example 3

Preparation of (2E)-5-Methyl-2-(1-methylethenyl)-2, 4-hexadienal (1) (Dehydrolavandulal) by Self-Aldol Condensation of 3-Methyl-2-butenal (Prenyl Aldehyde) in the Presence of Propionic Acid, Tert-Octylamine, and Sodium Sulfate at 20° C.

174 mg (2.07 mmol) of 3-methyl-2-butenal, 1.00 mL of heptane, 1.00 mL of tert-amyl alcohol, 0.20 mL (2.7 mmol) of propionic acid (99+%), 58 mg of anhydrous sodium sulfate (granular), and 17 mg of tert-octylamine were added to a stoppered 25 mL, 1-neck reaction flask containing a TEFLON®-coated spin bar. The reaction mixture was stirred at room temperature for 4 days, then diluted with 10 mL of hexane. 600 mg of anhydrous potassium carbonate was added, and the mixture subsequently was stirred at room temperature for 45 minutes to neutralize propionic acid. The product then was isolated in the manner described in Example 2 to afford 69 mg of dehydrolavandulal (1), dehydrocitral (2), and 4,6,6-trimethyl-1,3-cyclohexadiene-1-carboxaldehyde (3) in a ratio of 83:10:7, respectively. Approximately 30% of this product mixture was the N-tert-octyl imine derivative of 3-methyl-2-butenal, which can be removed from the polyenals according to the hydrolysis procedure described in Example 4.

Additional carboxylic acid catalysts were found to be suitable for performing the self aldol reaction. For example, the carboxylic acid catalyst can be insoluble in the reaction mixture. Replacement of propionic acid with AMBERLITE® IRC-50 ion exchange resin (weakly acidic resin, 20-50 mesh) in 1:1 (v/v) heptane:tert-amyl alcohol with a catalytic amount of tert-octylamine at 20° C. also yielded the self-aldol condensation products of 3-methyl-2-butenal. Use of AMBERLITE® as compared to propionic acid was found to decrease the rate of reaction. In the absence of propionic acid (or a compound of comparable acidity), the self-aldol condensation of 3-methyl-2-butenal proceeds very slowly or does not appreciably occur.

Example 4

Purification of (2E)-5-Methyl-2-(1-methylethenyl)-2, 4-hexadienal (1) (Dehydrolavandulal), (2E,4E)-3,7-Dimethyl-2,4,6-octatrienal (2) (Dehydrocitral), and 4,6,6-Trimethyl-1,3-cyclohexadiene-1-carboxaldehyde (3)

69 mg of a mixture of dehydrolavandulal (1), dehydrocitral (2), 4,6,6-trimethyl-1,3-cyclohexadiene-1-carboxaldehyde (3), and the N-tert-octyl imine derivative of 3-methyl-2-butenal, prepared as described in Example 3, was dissolved in 1.0 mL of toluene (A.C.S. reagent-grade) and then mixed with 2.0 mL of a solution of sodium acetate (400 mg) dissolved in 1:1 (v/v) water:glacial acetic acid. This heterogeneous mixture was stirred vigorously at room temperature for 2 hours, after which it was diluted with 20 mL of 3:1 (v/v) hexane: dichloromethane. The organic layer then was washed in successive order with 20 mL of 5% (w/v) aqueous NaCl mixed with 2.0 mL of 2M aqueous HCl; 20 mL of 10% (w/v) aqueous NaCl; 15 mL of saturated aqueous sodium bicarbonate; and 15 mL of saturated brine. The organic layer then was dried over anhydrous magnesium sulfate and subsequently filtered. Removal of the volatile organic solvents by evaporation at reduced pressure, followed by removal of 3-methyl-2-butenal at room temperature under high vacuum (0.25 mmHg), afforded 49 mg (28% conversion, based on the amount of 3-methyl-2-butenal used in Example 3) of dehydrolavandulal (1), dehydrocitral (2), and 4,6,6-trimethyl-1,3-cyclohexadiene-1-carboxaldehyde (3) in a ratio of 25:3:2 respectively. The latter ratio of products was determined by integration of the NMR signal exhibited by the aldehydic proton in each of these polyenals (cited in Example 1). The formation of dehydrolavandulal (1) as the major product (>83% of the polyenal mixture) was unexpected since it was not detected in previous studies of the self-aldol condensation of 3-methyl-2-butenal. For example, see: D. Cahard, et al., Tetrahedron Lett., 39, 7093 (1998).

Example 5

Preparation of 2-Isopropyl-5-methyl-1-hexanol (Tetrahydrolavandulol)

A solution of 35 mg (0.23 mmole) of dehydrolavandulal (1) (>83% pure; produced in accordance with Example 4) and 25 mg (0.66 mmole) of sodium borohydride in 2.0 mL of ethyl alcohol was stirred at room temperature for 60 minutes, after which 0.50 mL of water was added to the mixture and stirring was continued for an additional 5 minutes. After dilution of the mixture with 25 mL of 4:1 (v/v) hexane:dichloromethane, the organic layer was washed in successive order with 20 mL portions of 10% (w/v) aqueous NaCl and saturated brine. The organic layer then was dried over anhydrous magnesium sulfate and subsequently filtered. Removal of the volatile organic solvents by evaporation at reduced pressure afforded 29 mg (82% yield) of (2E)-5-methyl-2-(1-methylethenyl)-2, 4-hexadien-1-ol (dehydrolavandulol), accompanied by minor amounts of the alcohols obtained via reduction of the dehydrocitral (2) and 4,6,6-trimethyl-1,3-cyclohexadiene-1-carboxaldehyde (3) present in the starting material. The identity of dehydrolavandulol was ascertained by proton NMR analysis (recorded in $CDCl_3$ solution at 300 MHz). The latter spectrum exhibited a doublet (J=11.4 Hz) at δ 6.25 (vinyl H at $C_3$); a broad doublet (J=11.4 Hz) at δ 6.06 (vinyl H at $C_4$); broad singlet at δ 5.15 and δ 4.86 ($C=CH_2$); a broad singlet at δ 4.19 ($CH_2O$); a broad singlet at δ 1.89 (3H, vinyl $CH_3$); and a singlet at δ 1.79 (6H, 2 $CH_3$ groups).

In lieu of catalytic hydrogenation using $H_2$/Pd, the carbon-carbon double bonds in the above trienol were saturated in accordance with a procedure reported by Sala, et al., *Tetrahedron Lett.*, 25, 4565 (1984). The latter procedure involved slow addition (over a period of 4 hours) of an aqueous solution containing a large excess of sodium hypophosphite hydrate to a mixture of the trienol in ethanol containing a catalytic amount of 10% Pd—C at 50° C. The major product obtained by this procedure was shown by proton NMR analysis to be 2-isopropyl-5-methyl-1-hexanol (tetrahydrolavandulol). The latter proton NMR spectrum was compared with that exhibited by an authentic sample of tetrahydrolavandulol, which can be viewed on the Spectral Data Base System (SDBS) maintained by the Japanese National Institute of Advanced Industrial Science and Technology.

Example 6

Self-Aldol Condensation of 3-Methyl-2-Butenal in a Concentrated Solution of 1:1 (v/v) tert-Amyl Alcohol:Octane at 45° C.

92 mg (1.1 mmol) of 3-methyl-2-butenal, 0.25 mL of octane, 0.25 mL of tert-amyl alcohol, a trace (less than 1 mg) of the antioxidant BHT, 14 mg (0.11 mmol) of benzoic acid, 43 mg of anhydrous sodium sulfate, 10 microliters (0.06 mmol) of tert-octylamine, and a TEFLON®-coated spin bar were added to a 25 mL, 1-neck reaction flask fitted with an adapter connected to an apparatus similar to that described by Johnson and Schneider [*Org. Synth.*, 30, 18 (1950)] so that the mixture in the flask could be protected from atmospheric conditions throughout the course of the reaction.

After purging the system briefly with a stream of nitrogen gas, the mixture was heated (43-45° C., external oil bath temperature) for 18 hours. After cooling the mixture to room temperature, 5 mL of hexane and 50 mg of anhydrous potassium carbonate were added to the flask, and the mixture subsequently was stirred at room temperature for 60 minutes to neutralize the benzoic acid. The product then was isolated by filtering off any solid material through a small pad of HYFLO SUPER-CEL®, followed by removal of the volatile organic solvents by evaporation at reduced pressure. Subsequent removal of unreacted 3-methyl-2-butenal and trace amounts of tert-octylamine at room temperature under high vacuum (0.25 mmHg) afforded 38 mg (approximately 40% conversion) of a mixture of products, the identity and ratio of which were ascertained by proton NMR analysis (recorded in CDCl$_3$ solution at 300 MHz).

The polyenal mixture consisted of dehydrolavandulal (1), dehydrocitral (2), and 4,6,6-trimethyl-1,3-cyclohexadiene-1-carboxaldehyde (3) in a 10:2:1 ratio, respectively. Approximately 45% of the crude product consisted of the N-tert-octyl imine derivative of 3-methyl-2-butenal. When the reaction temperature was increased to 70° C., the percent conversion was improved (greater than 65% after 15 hours) and the amount of recovered 3-methyl-2-butenal imine derivative was significantly reduced. The ratio of dehydrolavandulal (1) to dehydrocitral (2), however, was less favorable (approximately 3:1).

Although the formation of dehydrocitral (2) relative to dehydrolavandulal (1) increased slightly at higher temperature, the process is still attractive for the manufacture of fragrance chemicals since these two compounds comprised greater than 90% of the product mixture and can be separated by fractional distillation. Exhaustive hydrogenation of dehydrocitral (2) affords 3,7-dimethyloctan-1-ol (tetrahydrogeraniol), which possesses a rose petal-like odor and is often used to perfume household products.

Example 7

Self-Aldol Condensation of 3-Methyl-2-butenal in the Presence of a Carboxylic Acid and a Secondary Amine 86 mg (1.02 mmol) of 3-methyl-2-butenal, 1.00 mL of tetrahydrofuran (99.5+%; purchased from Aldrich Chemical Co., Milwaukee, Wis.), 1.00 mL of toluene, a trace (less than 1 mg) of the antioxidant BHT, 16 mg (0.13 mmol) of benzoic acid, 90 mg of anhydrous sodium sulfate (granular), 10 microliters (0.057 mmol) of diisobutylamine (purchased from Aldrich Chemical Co., Milwaukee, Wis.), and a TEFLON®-coated spin bar were added to a 15 mL, 1-neck stoppered reaction flask. The mixture was stirred at room temperature for 18 hours, after which the mixture was diluted with 4.0 mL of hexane, and 50 mg of anhydrous potassium carbonate was added to the flask. This mixture subsequently was stirred at room temperature for 60 minutes to neutralize benzoic acid. The product then was isolated by filtering off any solid material through a small pad of HYFLO SUPER-CEL®, followed by removal of the volatile organic solvents by evaporation at reduced pressure. Subsequent removal of unreacted 3-methyl-2-butenal and small amounts of diisobutylamine at room temperature under high vacuum (0.25 mmHg) afforded 28 mg (approximately 32% conversion) of product shown by proton NMR analysis (recorded at 300 MHz in CDCl$_3$ solution) to contain only trace amounts (<2%) of dehydrolavandulal (1) and 4,6,6-trimethyl-1,3-cyclohexadiene-1-carboxaldehyde (3). The absence of the compound (3) was unexpected, because Watanabe, et al. in *J. Org. Chem.*, 71, 9458 (2006) reported that 3-methyl-2-butenal undergoes self-condensation in the presence of a stoichiometric amount of proline at room temperature to afford only 4,6,6-trimethyl-1,3-cyclohexadiene-1-carboxaldehyde (3).

The polyenal obtained in this process was a 3:1 mixture of 2E:2Z stereoisomers of dehydrocitral (2), accompanied by minor amounts of "enamine intermediates" involved in this self-aldol process. The proton NMR spectrum of the (2E)-stereoisomer of dehydrocitral exhibited a doublet (J=8.1 Hz) at $\delta$10.10 (CH=O); a broad doublet (J=8.1 Hz) at $\delta$5.95 (vinyl H at C$_2$); a doublet (J=1.2 Hz) at $\delta$2.30 (CH$_3$ at C$_3$); and other peaks as reported in Example 1 (a doublet of doublets (J=15, 11 Hz) at $\delta$ 6.97 (vinyl H at C$_5$); a doublet (J=15 Hz) at $\delta$ 6.24 (vinyl H at C$_4$); a broad doublet (J=11 Hz) at $\delta$ 6.00 (vinyl H at C$_6$); overlapping broad singlets at $\delta$ 1.88 (two CH$_3$ groups at C$_7$)). The corresponding signals for the (2Z) stereoisomer were a doublet (J=8 Hz) at $\delta$ 10.19 (CH=O); a doublet (J=8 Hz) at $\delta$ 5.82 (vinyl H at C$_2$), and a doublet (J=1.2 Hz) at $\delta$ 2.12 (CH$_3$ at C$_3$).

Similar results were obtained when the self-aldol condensation of 3-methyl-2-butenal was conducted in 1:1 (v/v) tert-amyl alcohol:heptane containing catalytic amounts of both a carboxylic acid (e.g., benzoic acid or propionic acid) and a secondary amine (e.g., morpholine or diisobutylamine). Although the presence of a drying agent (e.g., Na$_2$SO$_4$) was not essential, in the absence of either the secondary amine or the carboxylic acid little to no aldol condensation product was formed.

Attempts to increase the percent conversion of 3-methyl-2-butenal to dehydrocitral (2) higher than approximately 35% led to the gradual formation of "C-15 adducts," as characterized by a doublet (J=7.8 Hz) at $\delta$ 10.11 (CH=O) and an increase in the number of vinyl hydrogen signals. Without subscribing to any particular mechanism, as the concentration of the product dehydrocitral (2) increased, C-15 adducts formed by reaction of dehydrocitral (2) with the enamine derivative of 3-methyl-2-butenal. Despite the moderate percent conversion (35%), the purity of dehydrocitral (2) obtained in this process is high. As a result this method represents an attractive route for the production of costly safranal, especially since unreacted 3-methyl-2-butenal is easily recycled.

Example 8

Self-Aldol Condensation of 3-Methyl-2-butenal in the Presence of a Carboxylic Acid and a Tertiary Amine In accordance with the procedure described in Example 1, a mixture of 97 mg (1.15 mmol) of 3-methyl-2-butenal, 1.00 mL of tetrahydrofuran (99.5+%, inhibited with 25 ppm of BHT), 1.00 mL of toluene (A.C.S. reagent-grade), 0.10 mL (0.57 mmol) of nonanoic acid, 250 mg of anhydrous sodium sulfate (granular), and 40 microliters (0.23 mmol) of N-diisopropylethylamine was heated at gentle reflux (65-67° C., external oil bath temperature) for 3 hours. After cooling the mixture to room temperature, 4.0 mL of hexane and 150 mg of anhydrous potassium carbonate were added to the flask; and the mixture subsequently was stirred at room temperature for 60 minutes to neutralize nonanoic acid. The product then was isolated as described in the procedure of Example 1, affording 8 mg of material. Proton NMR analysis of the latter material showed that it was a mixture of dehydrocitral (2), dehydrolavandulal (1), and 4,6,6-trimethyl-1,3-cyclohexadiene-1-carboxaldehyde(3) in a 6:1:1 ratio, respectively, based on integration of the aldehydic proton signals.

What is claimed is:

1. A method for preparing a 1,2-self aldol condensation product of 3-methyl-2-butenal comprising:
    reacting 3-methyl-2-butenal in the presence of a weak acid and an amine at a temperature of 10° C. or higher under conditions sufficient to form a 1,2-self aldol condensation product of 3-methyl-2-butenal.

2. The method of claim 1, wherein the amine comprises a primary amine, and an α-1,2-condensation product of 3-methyl-2-butenal is formed.

3. The method of claim 1, wherein the amine comprises a secondary amine or a tertiary amine, and a γ-1,2-condensation product of 3-methyl-2-butenal is formed.

4. The method of claim 1, wherein the weak acid has a $pK_a$ relative to water of about 2 to about 6.

5. The method of claim 1, wherein the weak acid comprises a carboxylic acid having a $pK_a$ relative to water of about 2 to about 6.

6. The method of claim 5, wherein the carboxylic acid comprises an alkanoic acid having a formula $RCO_2H$, wherein R is $C_1$ to $C_{17}$ alkyl.

7. The method of claim 6, wherein the alkanoic acid is selected from the group consisting of acetic acid, propionic acid, butanoic acid, pentanoic acid, hexanoic acid, heptanoic acid, octanoic acid, nonanoic acid, decanoic acid, dodecanoic acid, tetradecanoic acid, hexadecanoic acid, and mixtures thereof.

8. The method of claim 5, wherein the carboxylic acid comprises an aromatic carboxylic acid.

9. The method of claim 8, wherein the aromatic carboxylic acid comprises benzoic acid.

10. The method of claim 5, wherein the carboxylic acid comprises an alkanedioic acid.

11. The method of claim 10, wherein the alkanedioic acid is selected from the group consisting of hexanedioic acid, tartaric acid, and mixtures thereof.

12. The method of claim 1, wherein the weak acid comprises a weakly acidic ion-exchange resin.

13. The method of claim 1, wherein the amine comprises an alkyl primary amine.

14. The method of claim 1, wherein the amine comprises an alkyl primary amine having a formula $H_2NR^1$, wherein $R^1$ is selected from the group consisting of secondary alkyl, cycloalkyl, and tertiary alkyl.

15. The method of claim 14, wherein the alkyl primary amine is selected from the group consisting of tert-octylamine, tert-butylamine, cyclohexylamine, and mixtures thereof.

16. The method of claim 1, wherein the amine comprises a dialkyl secondary amine.

17. The method of claim 16, wherein the dialkyl secondary amine is selected from the group consisting of diethylamine, diisobutylamine, morpholine, pyrrolidine, and mixtures thereof.

18. The method of claim 1, wherein the amine comprises a trialkyl tertiary amine.

19. The method of claim 18, wherein the trialkyl tertiary amine is selected from the group consisting of triethylamine, diisopropylethylamine, and mixtures thereof.

20. The method of claim 2, wherein (2E)-5-methyl-2-(1-methylethenyl)-2,4-hexadienal is formed.

21. The method of claim 3, wherein (2E,4E)-3,7-dimethyl-2,4,6-octatrienal is formed.

22. A method for preparing a 1,2-self aldol condensation product comprising:
    reacting an α,β-unsaturated aldehyde having two γ-hydrogens in the presence of a weak acid and an amine at a temperature of 10° C. or higher under conditions sufficient to form a 1,2-self aldol condensation product.

23. A method for preparing a 1,2-self aldol condensation product comprising:
    reacting an α,β-unsaturated aldehyde having at least two γ-hydrogens in the presence of a weak acid and an amine at a temperature of 10° C. or higher under conditions sufficient to form a 1,2-self aldol condensation product, wherein the α,β-unsaturated aldehyde having at least two γ-hydrogens is selected from the group consisting of trans-2-methyl-2-butenal and (E)-2-pentenal.

* * * * *